United States Patent [19]
Rieder et al.

[11] Patent Number: 5,851,221
[45] Date of Patent: Dec. 22, 1998

[54] ATTACHMENT APPARATUS AND METHOD FOR AN IMPLANTABLE MEDICAL DEVICE

[75] Inventors: Eric M. Rieder, Alton; Frank Gonzalez, Brampton; Randal C. Schulhauser, Brulington, all of Canada; Bryan Zart, Shakopee, Minn.

[73] Assignee: Medtronic Inc., Minneapolis, Minn.

[21] Appl. No.: 905,093

[22] Filed: Aug. 1, 1997

Related U.S. Application Data

[60] Provisional application No. 60/032,780 Dec. 5, 1996.
[51] Int. Cl.$^6$ .................................................. A61N 1/375
[52] U.S. Cl. ................................................................ 607/93
[58] Field of Search ................................ 607/1, 2, 9, 38

[56] References Cited

U.S. PATENT DOCUMENTS

| | | | |
|---|---|---|---|
| 4,041,956 | 8/1977 | Purdy et al. | 128/419 P |
| 4,142,532 | 3/1979 | Ware | 128/419 P |
| 4,182,345 | 1/1980 | Grose | 128/419 P |
| 4,243,042 | 1/1981 | Ware | 128/419 P |
| 4,248,237 | 2/1981 | Kenny | 128/419 P |
| 4,314,562 | 2/1982 | Ware | 128/419 P |
| 5,070,605 | 12/1991 | Daglow et al. | 29/842 |
| 5,086,773 | 2/1992 | Ware | 128/419 P |
| 5,207,218 | 5/1993 | Carpentier et al. | 128/419 P |
| 5,431,695 | 7/1995 | Wiklund et al. | 607/36 |
| 5,456,698 | 10/1995 | Byland et al. | 607/36 |
| 5,522,861 | 6/1996 | Sikorski et al. | 607/36 |
| 5,535,097 | 7/1996 | Ruben et al. | 361/736 |

OTHER PUBLICATIONS

U.S. Patent Application filed on even date herewith entitled, "Attachment Apparatus and Method for an Implantable Medical Device Employing Ultrasonic Energy," to Haeg et al., p. 4, lines 24–27. (P–4590).

"Designing Parts for Ultrasonic Welding,", Branson Ultrasonics Corporation, Danbury, CT, 1975.

"TechnoLog—Today's Source for Plastics Joingin Technology," Branson Ultrasonics, Corporation, Danbury, CT, 1992.

"Ultrasonic Staking", Branson Ultrasonics Corporation, Danbury, CT, 1980.

*Primary Examiner*—William E. Kamm
*Attorney, Agent, or Firm*—Thomas F. Woods; Harold R. Patton

[57] ABSTRACT

An implantable medical device of the type formed of a hermetically sealed enclosure attached on a enclosure attachment surface thereof to a module attachment surface of a pre-formed header module is disclosed. The pre-formed header module is attached to the enclosure attachment surface through use of a retention structure extending away from the enclosure surface into proximity with a portion of the pre-formed header module when the enclosure and module attachment surfaces are aligned with respect to one another. The retention structure comprises a bendable member that is bent from an initial position allowing the pre-formed header module to be seated with respect to the hermetically sealed enclosure to a retention position making an attachment against a bend engaging portion of the pre-formed header module. The bendable member is the free end portion of an attachment tab having a tab base attached at a predetermined location of the hermetically sealed enclosure such that the upstanding attachment tab extends in a predetermined direction away from the enclosure surface and the free end of the attachment tab is bendable laterally with respect to the predetermined direction against the bend engaging portion. Adhesive is then applied to the retention mechanism and the space between the enclosure attachment surface and the module attachment surface.

28 Claims, 8 Drawing Sheets

ATTACHMENT APPARATUS AND METHOD FOR AN IMPLANTABLE MEDICAL DEVICE

PRIORITY CLAIM

This application claims priority and other benefits from U.S. Provisional patent application Ser. No. 60/032,780, now abandoned, entitled Insertable Loop Recorder and Method of Manufacture to Rieder, et al. filed Dec. 5, 1996.

CROSS-REFERENCE TO RELATED APPLICATIONS

Reference is hereby made to commonly assigned, co-pending U.S. patent application Ser. No. 08/904,601, filed Jul. 30, 1997, for ATTACHMENT APPARATUS AND METHOD FOR AN IMPLANTABLE MEDICAL DEVICE EMPLOYING ULTRASONIC ENERGY in the names of D. Haeg et al.

FIELD OF THE INVENTION

The present invention generally relates to implantable medical devices and particularly to the attachment of a pre-formed header module, e.g. a lead or catheter connector header module or an electrode bearing header module, etc., to a hermetically sealed enclosure of the implantable medical device, typically including electronic integrated circuits, batteries, electromechanical pumps, or the like.

BACKGROUND OF THE INVENTION

The earliest implantable medical devices, e.g., implantable cardiac pacemakers and other body tissue stimulating devices, were formed of an implantable pulse generator (IPG) and a set of electrical leads attached between the IPG and heart or body tissue to be paced or stimulated. Typically, the IPG electrical circuit was powered either by Hg—Zn batteries or by induction of energy transmitted transcutaneously from a skin surface RF power generator and supplied electrical pacing or stimulating pulses to the leads. The IPG batteries and circuits were encapsulated within an epoxy compound partly for ease of manufacture and to allow hydrogen emitted by the Hg—Zn batteries to escape. Electrical connector pins and rings, if present, were initially permanently attached to the circuits. Other early implantable medical devices, e.g. implantable monitors and cochlear implants or the like were also formed in somewhat the same manner.

Such early implantable cardiac pacemakers suffered very short useful lives due to moisture ingress through the epoxy and causing electrical dendritic growth across, and shorting of, adjacent points of the circuit, battery terminals, or discrete transistor terminals. In addition, pacing leads frequently failed due to conductor stress fractures, and batteries depleted prematurely for a variety of reasons.

In the 1960's, IPG connector assemblies were formed integrally with other IPG circuit components and embedded in an epoxy housing to enable attachment of a chosen lead to the IPG circuit for initial implant or defective lead replacement purposes. These integrally formed connector assemblies typically comprised at least one metal, electrical connector block encapsulated therein that were aligned in relation to an elongated lead end receptacle for receiving the proximal lead end. Each connector block was formed to have a bore to receive the lead connector pin or ring, depending on the type of lead intended to be used, and a threaded cross bore receiving a trapped set screw. The connector block(s) was electrically directly attached to the IPG circuit. A silicone rubber suture boot was placed in the mold so that it's bore would be aligned with the elongated receptacle. The entire IPG including these connector assembly components, was then encapsulated in epoxy.

In use, the proximal lead connector end(s) was inserted into the appropriate lead connector receptacle until the lead connector pin or ring was received in the bore of the connector block(s). Then, the set screw was tightened by a hex wrench to maintain the firm electrical and mechanical attachment, and the opening through the molded epoxy housing to access the set screw was sealed. Sutures were tied around the suture boot(s) to seal it against the lead body.

Since about the mid-1970's, hermetically sealed, lithium batteries and miniaturized, digital and analog, integrated circuits (ICs) have been used in implantable medical devices, particularly for implantable cardiac pacemaker and nerve stimulation IPGs. The ICs, batteries, and other components are enclosed in hermetically sealed metallic enclosures or "cans" separated from the connector assembly components. Electrical connection with the connector block(s) and/or other components of the connector assembly is obtained by use of electrical feedthroughs supporting feedthrough pins that extend through the hermetically sealed can.

In certain instances, the lead connector assembly components external to the hermetically sealed enclosure are still to this date attached to an attachment surface thereof using an in situ molding process to seal the connector assembly components and form the receptacle for a lead or catheter proximal end, etc. Very simply, in the formation of a lead connector assembly for a cardiac pacemaker IPG, for example, the connector block(s) and feedthrough pin(s) are welded together and laid out in a mold with respect to any other associated components and mold plugs. An encapsulating compound is injected into the mold to form the connector header assembly molded to the IPG attachment surface as described, for example, in U.S. Pat. No. 4,041, 956. This approach is time consuming and not terribly precise. If the resulting connector header assembly fails to meet dimensional tolerances or other quality requirements, it is difficult to rework the IPG.

In 1979, the MEDTRONIC® SPECTRAX® cardiac pacemaker IPGs were introduced having the digital and analog or hybrid IC's and lithium batteries forming the pacing circuit enclosed within a hermetically sealed titanium enclosure having feedthroughs extending through an enclosure attachment surface thereof. Such an assembly of these components is disclosed in commonly assigned U.S. Pat. Nos. 4,142,532 and 4,182,345, incorporated herein by reference.

The lead connector assembly, in this case and as used in IPG models to the present time by Medtronic, Inc., is manufactured as a separate pre-formed connector header module that encloses connector components and is attached to an enclosure attachment surface of the hermetically sealed enclosure and to the feedthrough pins. The connector header module is molded of a thermoplastic elastomer, e.g., a medical grade polyurethane, with an outer module surface and a number of receptacles and channels within it that in some instances are accessible through windows extending to the module surface. The connector header module receives the electrical connector block(s) in connector block receptacle(s) such that the connector block bore(s) is aligned with elongated lead connector receptacle(s) for receiving the proximal lead connector end assembly(s). In the typical design, each such connector block is formed with a threaded cross bore receiving a trapped set screw as described above. Each set screw of each connector block in a connector block receptacle is also aligned with a septum receptacle for receiving a silicone rubber set screw septum. The preformed connector header module is formed with pin channel (s) for directing the feedthrough pin(s) into contact with the respective connector block(s) and with window(s) to allow the connector block(s) and septum(s) to be inserted into their respective receptacle(s). In each case, the connector block receptacle window or a further window to the module surface is provided for allowing the feedthrough pin end to be welded to the connector block. The windows(s) and pin channel(s) are typically back filled with a medical grade silicone adhesive after the welding step and attachment of the connector header module to the hermetically sealed enclosure.

As a general rule, the connector header module formed as described above, has to satisfy very tight tolerances and remain dimensionally stable over a long time period of implantation within the hostile environment of the human body. Any substantial initial or time-induced misalignment of the lead connector receptacle bore(s) extending through the molded module housing and the connector block bore(s) can make initial attachment or removal and replacement of a lead connector end impossible or unreliable.

During the attachment of the connector header module to the hermetically sealed enclosure, medical grade adhesive may be employed to adhere the module attachment surface with the enclosure attachment surface. During the curing of the adhesive, it is necessary to ensure that the attachment surfaces are not disturbed. It has been proposed to employ mechanical attachment mechanisms as a substitute for or in addition to the use of the medical grade adhesive between the attachment surfaces to provide stability and strength. Such mechanical attachment mechanisms that have been proposed for use or actually used either alone or with adhesive take a variety of forms, e.g., the forms shown in commonly assigned U.S. Pat. Nos. 4,142,532 and 4,182,345, both incorporated herein by reference in their respective entireties. While these approaches have merit, they require use of additional, precision piece parts and assembly steps that can add to the cost and time spent in assembling the connector header module with the hermetically sealed enclosure.

In a further current approach employing both adhesive and temporary mechanical fixation, tab channels are formed in the connector header module to receive upstanding attachment tabs that are welded to the enclosure attachment surface to extend outward therefrom. The upstanding attachment tabs are formed with hooks at their ends that snap into engagement with undercuts that are intentionally formed in the tab channels. Adhesive is applied to the mating attachment surfaces and into the tab channels. This mechanical attachment provides a temporary fixation with relatively low resistance to dislodgement for several hours until adhesive applied to the mating attachment surfaces sets up.

Finally, it should be noted that it has been recently proposed to form the connector header module as part of a shroud surrounding and adhering to the rim of the hermetically sealed enclosure in order to simplify the assembly by reducing the number of parts, assembly steps and required tolerances. Such a configuration is shown in commonly assigned U.S. Pat. Nos. 5,535,097, 5,522,861, 5,456,698 and 5,431,695, all incorporated herein by reference in their respective entireties. In this configuration, the shroud is preferably formed of a flexible silicon rubber, and pacing leads may be attached and replaced in the normal manner for an implantable pacing system. However, the use of silicone rubber has its own disadvantages related to dimensional instability and lack of rigidity, general design aesthetics, and potential discoloration of the silicone rubber during storage and sterilization which contribute to lack of market acceptance.

The adhesion force or "peel and pull strength" of the connector header module with the hermetically sealed enclosure at the mating attachment surfaces is important both during the adhesive curing time and in later chronic implantation of the implantable medical device. The pull strength is the separation force, specified in pounds, applied perpendicularly to the plane of the header module and enclosure attachment surfaces sufficient to pull the header module away from the hermetically sealed enclosure. The peel strength is the separation force, specified in pounds, applied laterally against a major side of the header module sufficient to break the attachment laterally. The curing or drying of adhesive between the mating attachment surfaces to establish a specified peel and pull strength takes time, and this delay in manufacturing is undesirable. Moreover, the peel and pull strength that can be achieved is limited by the areas of contact of the mating attachment surfaces. Consequently, a need remains for an improved mechanical attachment mechanism and method that avoids undue delay and provides enhanced peel and pull strength upon completing the attachment. As will become apparent from the following, the present invention satisfies that need.

Certain implantable medical devices other than IPGs also require the attachment of a pre-formed header module with a hermetically sealed enclosure. Such pre-formed header modules do not include lead connector components and connector end receptacles. Similar considerations of simplified manufacture, reduced cost and enhanced peel and pull strength also apply to the assembly of such preformed header modules and hermetically sealed enclosures.

SUMMARY OF THE INVENTION

It is an object of the present invention to solve these problems identified with prior art methods and mechanisms for attaching a preformed header module to a hermetically sealed enclosure of an implantable medical device.

A number of advantages are achieved in the practice of the present invention. A mechanical attachment is effected quickly employing a simple retention structure and minimal attachment steps. The retention structure employs a minimal number of parts all of which are found either attached to the hermetically sealed enclosure or in the header module and does not require the use of any additional parts that must be combined with or attached to either of these major parts. The retention structure self aligns and ensures that the preformed header module is aligned precisely to the hermetically sealed enclosure. A relatively high peel and pull strength is achieved Immediately following the mechanical attachment steps which can be readily automated.

Adhesive attachment can be combined with the mechanical attachment to increase the peel and pull strength. The mechanically attached header module and hermetically sealed enclosure assembly can be handled during the adhesive drying time without a significant risk that they will become mis-aligned or separated before the adhesive dries. The mechanical attachment is immediately secure and does not require a long curing time of the adhesive. A relatively viscous body implantable grade adhesive may therefore be employed to seal the interface space between the mating module and enclosure attachment surfaces and channels thereto. In this way, irregularities in the mating attachment surfaces can be sealed and internal channels and spaces within the header module housing can be filled.

The pre-formed header module is attached to the enclosure attachment surface through use of a cooperative retention structure of the pre-formed header module and the hermetically sealed enclosure that are engaged when the enclosure and module attachment surfaces are aligned with respect to one another. The retention structure comprises a bendable member of the hermetically sealed enclosure and a bend engaging portion of the header module. The mechanical attachment is effected by bending the bendable member from an initial position allowing the pre-formed header module attachment surface to be seated with respect to the hermetically sealed enclosure attachment surface. The bendable member is bent to a retention position making the attachment against the bend engaging portion of the pre-formed header module.

Preferably, the bendable member is the free end portion of an attachment tab having a tab base attached at a predetermined location of the hermetically sealed enclosure such that the upstanding attachment tab extends in a predetermined direction away from the enclosure surface and the free end of the attachment tab is bendable laterally with respect to the predetermined direction against the bend engaging portion. Preferably, an implantable grade adhesive is then applied to the retention mechanism and the space between the enclosure attachment surface and the module attachment surface to seal the components of the header module and strengthen the attachment.

BRIEF DESCRIPTION OF THE DRAWINGS

These and other objects, advantages and features of the present invention will be appreciated as the same becomes better understood by reference to the following detailed description of the preferred embodiment of the invention when considered in connection with the accompanying drawings, in which like numbered reference numbers designate like parts throughout the figures thereof, and wherein.

The drawing figures are not all necessarily to scale.

DETAILED DESCRIPTION OF THE PREFERRED EMBODIMENTS

The preferred embodiments relate to use of the mechanism and method summarized above to attach a pre-formed header module attachment surface with a hermetically sealed enclosure attachment surface in the manufacture of an implantable medical device. Such implantable medical devices include implantable drug dispensers, IPGs (including cardiac pacemakers, pacemaker-cardioverterdefibrillators, nerve, muscle and neurological stimulators, cardiomyostimulators, etc.), implantable cardiac signal monitors and recorders and the like. Virtually all MEDTRONIC® electronic implantable medical devices that require attachment of a hermetically sealed power supply and circuitry with an interchangeable catheter or electrical lead or the like employ such a general configuration of a hermetically sealed enclosure and a pre-formed header module thereto.

In a first illustrated preferred embodiment, the attachment mechanism and method is used to attach a cardiac signal sense electrode bearing header module to a hermetically sealed cardiac signal monitor. In a further illustrated embodiment, the attachment mechanism and method are used to attach an IPG connector header module to a hermetically sealed enclosure of an IPG of the types listed above. At least in the case of IPGs and cardiac signal monitors, electrical feedthroughs extending through the hermetically sealed enclosure are coupled with components in the header module.

The attachment method and mechanism may also be used to attach an implantable drug pump catheter connector, header module to the hermetically sealed enclosure for the pump mechanism, battery and ICs controlling the pumping operation. However, those of skill in the art will be readily able to adapt the teachings found herein to other implantable medical devices. It will be understood that the term "header module" as used in the description and claims is comprehensive of any such pre-formed header module, including the electrode bearing header module of the first embodiment and the lead connector header module of the second embodiment.

Figure 1:
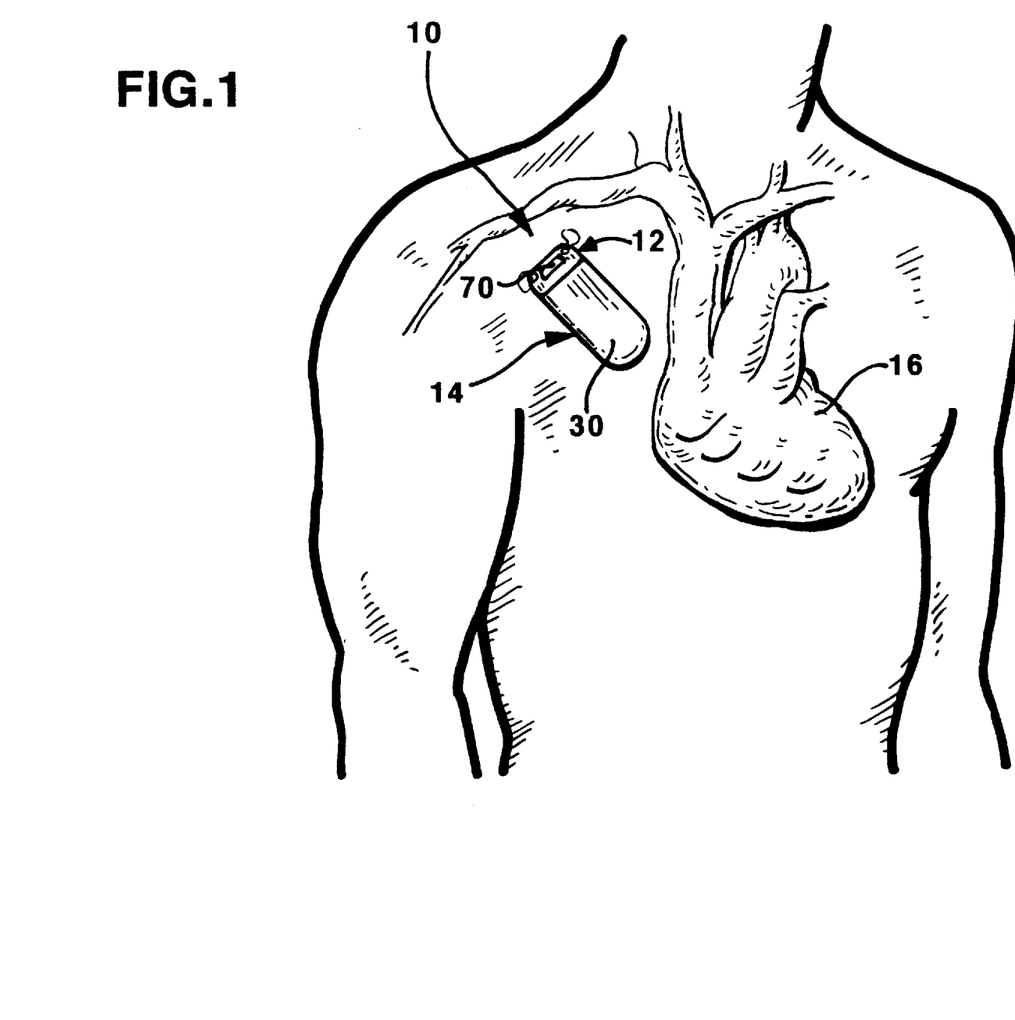
FIG. 1 is a simplified schematic view of an implantable cardiac signal monitor embodying the improved attachment of a preformed header module to a hermetically sealed enclosure in accordance with the present invention implanted in relation to a human heart.

FIG. 1 is a simplified schematic view of an implantable cardiac signal monitor 10 embodying the improved attachment of a pre-formed header module 12 to a hermetically sealed enclosure 14 in accordance with the first preferred embodiment of the present invention implanted in relation to a human heart 16. The cardiac signal monitor 10 includes at least header and can sense electrodes 70 and 30 across which electrical signals attendant to the depolarization and re-polarization of the heart 16 are sensed. The electrical circuitry within the cardiac signal monitor samples and records this electrogram of the heart over a number of heart cycles. The cardiac signal monitor 10 is sutured to subcutaneous tissue at a desired orientation of the electrodes 70 and 30 to the axis of the heart to detect and record the EGM for subsequent uplink telemetry transmission to an external programmer (not shown). FIG. 1 shows only one such orientation and is not necessarily to scale.

In general, the hermetically sealed enclosure 14 includes a lithium battery, circuitry that controls device operations and records arrhythmic EGM episodes, and a telemetry transceiver antenna and circuit that receives downlink telemetry commands from and transmits stored data in a telemetry uplink to the external programmer. The circuitry and memory may be implemented in discrete logic or a microcomputer based system with A/D conversion of sampled EGM amplitude values. The particular features and operations of the cardiac signal monitor are not of importance to the present invention. One exemplary operating system is described in commonly assigned, co-pending U.S. patent application Ser. No. 08/678,219, filed Jul. 11, 1996, for MINIMALLY INVASIVE IMPLANTABLE DEVICE FOR MONITORING PHYSIOLOGIC EVENTS, incorporated herein by reference.

Figure 2:
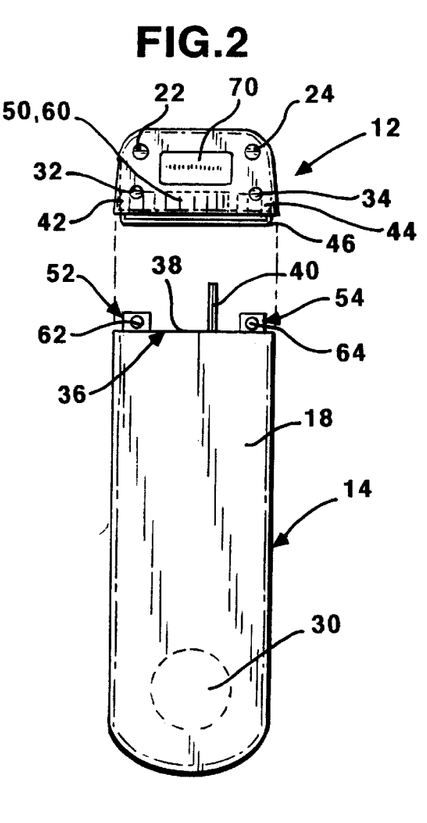
FIG. 2 is an exploded plan view of the header module in relation to the hermetically sealed enclosure of the implantable cardiac monitor of FIG. 1.
Figure 3:
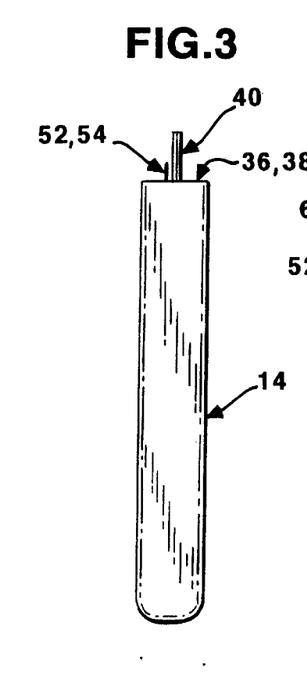
FIG. 3 is a side view of the hermetically sealed enclosure of the implantable cardiac monitor of FIG. 1.
Figure 4:
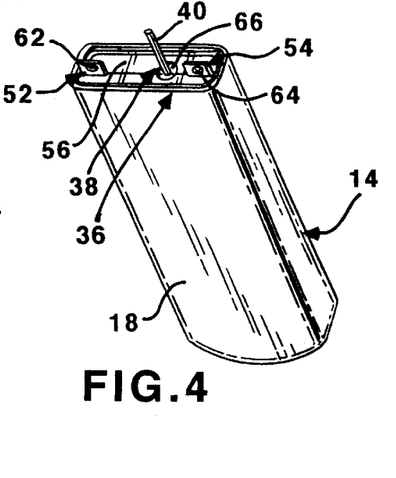
FIG. 4 is an isometric view toward the attachment surface of the hermetically sealed enclosure of the implantable cardiac monitor of FIG. 1.

This preferred embodiment involves the retention method and apparatus for attaching the pre-formed header module 12 to the hermetically sealed enclosure 14 at respective attachment surfaces thereof and providing electrical connection between the header electrode 20 and the EGM recording circuitry. FIG. 2 is an exploded plan view of the header module 12 in relation to the hermetically sealed enclosure 14. FIGS. 3 and 4 show the hermetically sealed enclosure 14 in side and isometric views. The hermetically sealed enclosure 14 is formed of an elongated and relatively flat metallic can 18 having a can lid formed across the end thereof and providing the hermetic enclosure attachment surface 38 bounded by a can and lid weld rim 36 extending around the respective peripheries thereof. An electrical feedthrough 66 is welded into the hermetic enclosure attachment surface 38 so that an electrically isolated feedthrough pin 40 extends across and outwardly therefrom.

It will be understood that the telemetry antenna, electrical circuitry and battery described above in general terms are mounted into a sub-assembly with appropriate insulators, spacers and circuit connections already made that is to be inserted into the can 18 and attached to the internally extending feedthrough pin 40. The sub-assembly is inserted into the can 18 and the can lid is welded to the can opening around the lid weld rim 36 to hermetically seal the components within the hermetically sealed enclosure 14.

Figure 10:
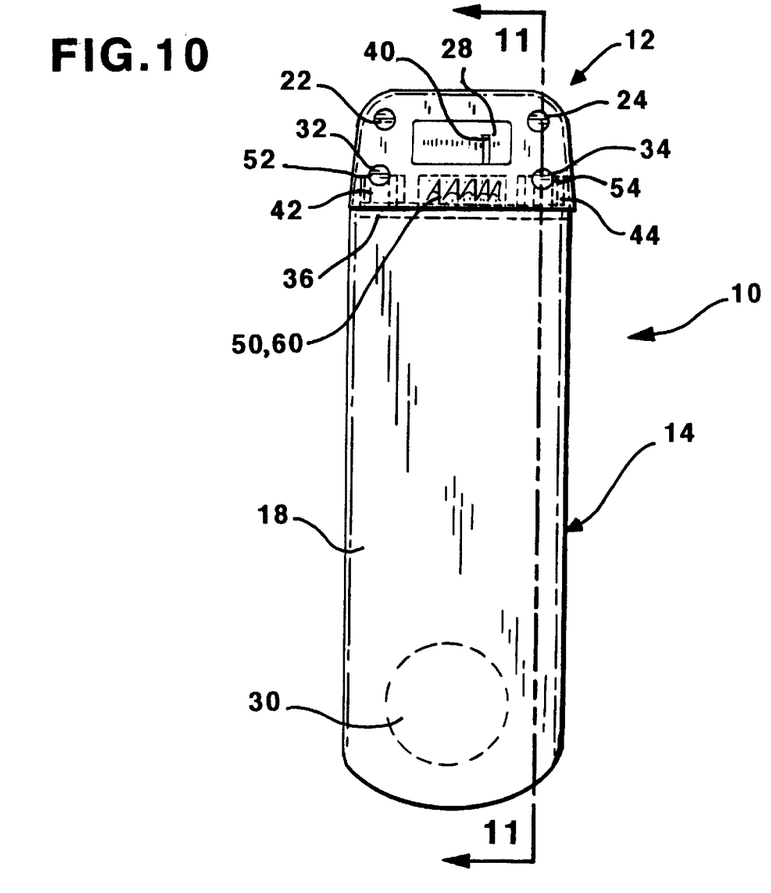
FIG. 10 is an elevation plan view of the seating of the header module attachment surface against the hermetically sealed enclosure attachment surface during the assembly of the implantable cardiac monitor of FIG. 1.

The cardiac signal monitor 10 includes a can electrode 30 formed by all or part of the exterior surface of metallic can 18 and at least one further header electrode 70 formed in the header module 12. The metallic can 18 and the further electrode 70 are electrically connected to sense amplifier circuit input terminals. The metallic can 18 can either be totally un-insulated so that the entire exterior surface operates as can electrode 30 or can be insulated in a pattern leaving a portion exposed as the can electrode 30 as shown in FIGS. 2 and 10.

Upstanding attachment tabs 52 and 54 having tab holes 62 and 64, respectively, formed therein extend outward of the can lid from opposite ends of a tab base 56. Tab base 56 is welded at a predetermined location to the can lid and provides part of the enclosure attachment surface 38 within the lid weld rim 36. As shown in FIGS. 2–4, the upstanding attachment tabs 52 and 54 are in line with one another and spaced apart from the upstanding feedthrough wire 40 in a predetermined manner that dimensionally corresponds to tab channels formed in the header module housing 20.

Figure 5:
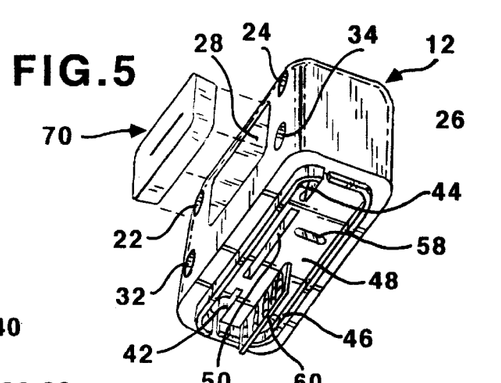
FIG. 5 is an exploded isometric view toward the attachment surface of the pre-formed header module of the implantable cardiac monitor of FIG. 1.
Figure 6:
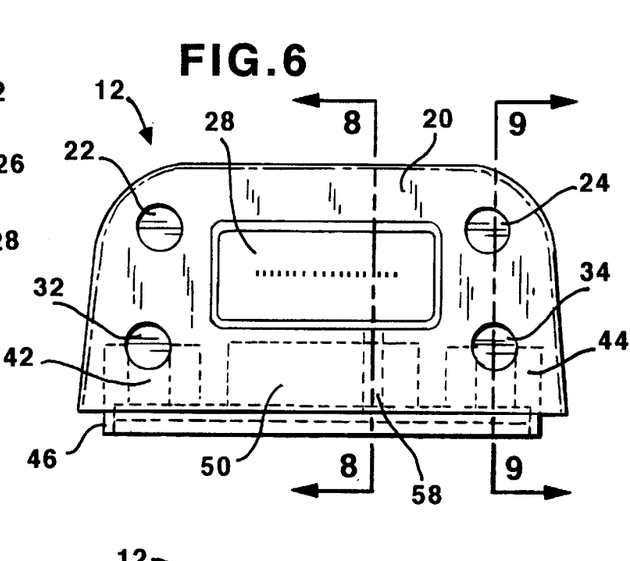
FIG. 6 is an elevation plan view of the header module of the implantable cardiac monitor of FIG. 1.
Figure 7:
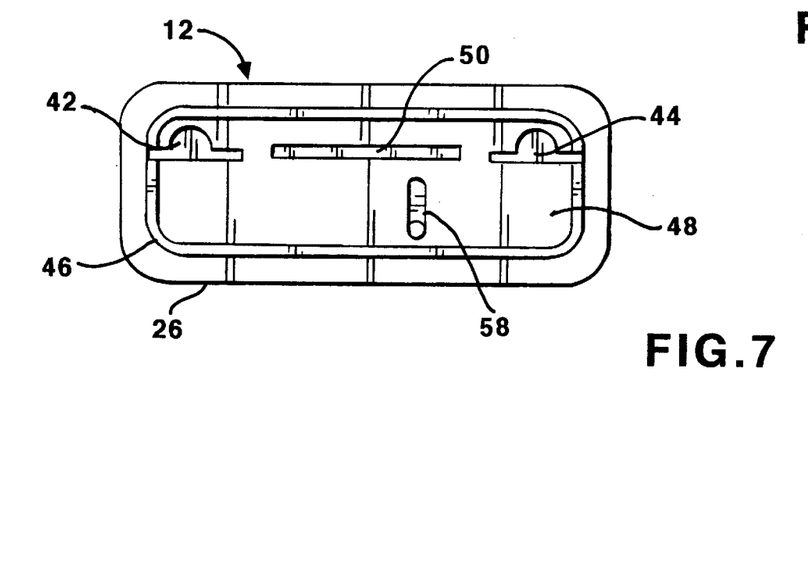
FIG. 7 is an attachment surface plan view of the header module of the implantable cardiac monitor of FIG. 1.

The header module 12 is molded of a rigid thermoplastic, e.g., a medical grade polyurethane, housing 20 having an exposed module surface 26 and a number of receptacles and channels shown in greater detail in FIGS. 6–9. Components including a header electrode 70 and radiopaque ID plate 60 fitted within respective electrode channel 28 and plate channel 50 of the housing 20 are shown in FIGS. 2, 5 and 10. FIGS. 10–14 show how the header module 12 is attached to the hermetically sealed enclosure 14 employing the upstanding tabs 52 and 54 and show a mass of adhesive 76 filling the space between the respective attachment surfaces and the channels leading thereto in the final assembly step.

The header module housing 20 is molded to have a pair of transversely extending suture bores or holes 22 and 24 extending across the width thereof through which sutures are passed into adjacent subcutaneous tissue when the cardiac signal monitor 10 is implanted as shown in FIG. 1. The suture holes 22 and 24 allow the electrodes 70 and 30 of the cardiac signal monitor 10 to be oriented at any desired angle to the heart.

An electrode channel 28 is formed extending transversely across the header module housing 20 located generally between the suture bores 22 and 24. The electrode channel 28 receives an electrode plate 70 inserted therein (in the broken line location designated 70' in FIG. 8) from one side opening so that an exposed electrode surface appears in a window on the other side of the header module housing 20. A pin receiving channel 58 is formed extending upward from module attachment surface 48 to intersect with the transverse electrode channel 28.

Figure 8:
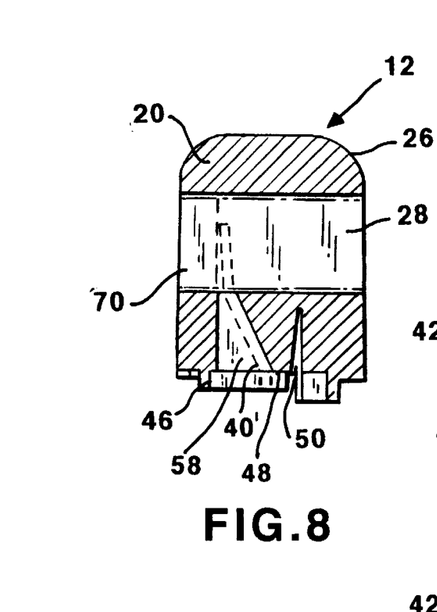
FIG. 8 is a side cross-section view of the header module of FIG. 6 taken along lines A—A.
Figure 9:
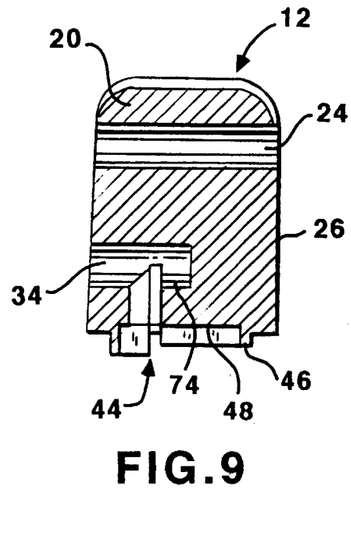
FIG. 9 is a side cross-section view of the header module of FIG. 6 taken along lines B—B.

Upon assembly of the header module 12 with the hermetically sealed enclosure 14 shown in FIG. 10, the feedthrough pin 40 is directed through the pin receiving channel 58 and deflected at an angle that intersects the interior surface of the electrode plate 70 as shown in the broken line deflection path 40' in FIG. 8. Then, in manufacture, the terminus of the feedthrough pin 40 can be welded to the interior surface of the electrode plate 70 through the electrode channel 28. Finally, the electrode channel 28 can be back filled with a spacer and adhesive or simply with a medical grade silicone adhesive typically used in implantable medical devices.

The module attachment surface 48 is bounded by a downwardly extending module rim 46 that fits within the lid weld rim 36 when the header module 12 is fitted onto the hermetically sealed enclosure 14 as shown in FIGS. 4–9. In that assembly depicted in FIG. 10, the module rim 46 spaces the module attachment surface 48 from the enclosure attachment surface 38. The module rim 46 serves in cooperation with weld rim 36 as an adhesive dam to direct adhesive flow into the space between the module attachment surface 48 and the enclosure attachment surface 38 as described below in reference to FIG. 14.

A pair of upwardly extending tab channels 42 and 44 are formed in the header module housing 20 that extend upward from the module attachment surface 48 in locations that are aligned with the locations of the upwardly extending attachment tabs 52 and 54, respectively. The tab channels 42 and 44 are shaped in height, width and thickness to receive the attachment tabs 52 and 54 when the header module 12 is seated against the hermetically sealed enclosure 14 as shown in FIGS. 10–14. In addition, the tab channels 42 and 44 are enlarged along one side to accommodate flow of adhesive through the tab channels 42 and 44 as described below.

A corresponding pair of cross-bores 32 and 34 are formed extending from one major side of the header exterior surface 26 partly across the header module housing 20 that transversely intersect the upper end portions of the tab channels 42 and 44, respectively. The cross-bores 32 and 34 are sized and located to intersect and provide access windows to the central upper end portions of the upstanding attachment tabs 52 and 54, respectively, within the cross-bores 32 and 34, respectively, to allow application of attachment force thereto. The cross-bores 32 and 34 extend laterally beyond the upper end portions of the tab channels 42 and 44 to provide bend engaging portions 72 and 74, respectively, at the intersecting edges thereof. The upper, central, end portions of the attachment tabs 52 and 54 are bent over the intersecting edges in the bend engaging portions 72 and 74. The cross-bores 32 and 24 also communicate with the space between the module attachment surface 48 and the header attachment surface 38 through the channels 42 and 44, respectively, for delivery of medical grade adhesive therein to fill them and increase the peel and pull strength.

FIGS. 11–14 depict the manufacturing steps of attaching the pre-formed header module 12 to the enclosure attachment surface 38 of the hermetically sealed enclosure 14. The depicted attachment steps follow the assembly and welding of the hermetically sealed enclosure 12 to its lid and the attachment of the tab base 56 to the lid to form the enclosure attachment surface 38 as described above. Moreover, the radiopaque ID plate 60 is fitted into the plate channel 50, and the header electrode 70 is fitted into the position 70' of the electrode channel 28. The illustrated attachment steps can either follow or precede the attachment of the terminus of the feedthrough pin 40 to the interior surface of the header electrode 70.

The upstanding attachment tabs 52 and 54 form bendable members of the retention structure extending away from the enclosure attachment surface 38 into proximity with the bend engaging portions 72 and 74 of the retention structure formed in the preformed header module 12. At least a central portion of the upper end portions of the attachment tabs that extend into the cross-bores 32 and 34 are bent over from the initial seated position of FIG. 11 to a retention position of FIGS. 12–14.

Figure 11:
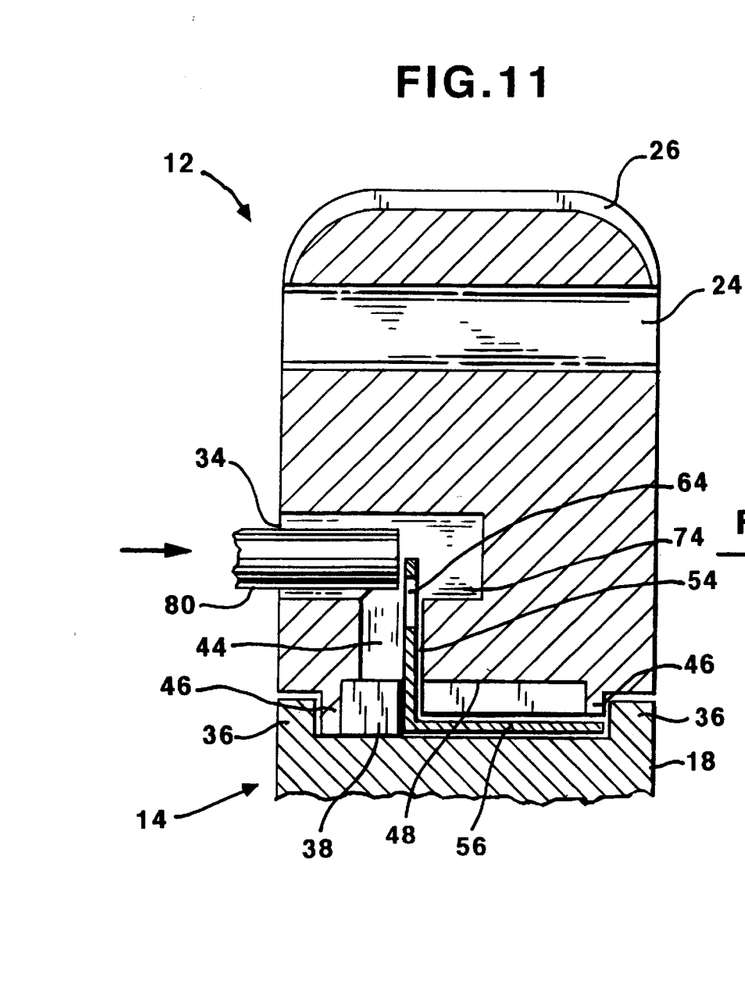
FIG. 11 is a partial side cross-section view of the header module and hermetically sealed enclosure taken along lines 11—11 of FIG. 10 showing the location of the upstanding attachment tab in a respective tab channel in the connector header module and the partial advancement of a staking tool through a cross-bore against an upstanding attachment tab.

FIG. 11 shows the initial steps of aligning and firmly seating the module attachment surface 48 against the enclosure attachment surface 38 such that the upstanding attachment tabs 52 and 54 are received in the respective tab channels 42 and 44, respectively. It will be understood that the feedthrough pin 40 is also extended through the feedthrough pin receiving channel 58 to bear against the interior surface of header electrode 70.

FIG. 11 also shows a bending tool 80 directed into an access window provided by cross-bore 34 and against the bendable member constituting the upper central portion of the attachment tab 54. In FIG. 11, the bendable members of the retention structure comprising the attachment tabs 52 and 54 extend upwardly away from the enclosure attachment surface 38 into proximity with the bend engaging portions 72 and 74, respectively. The bending tool 80 is poised to apply bending force to the upper end portion of attachment tab 54 to bend it into engagement with the bend engaging portion 74, in this illustrated case.

Figure 12:
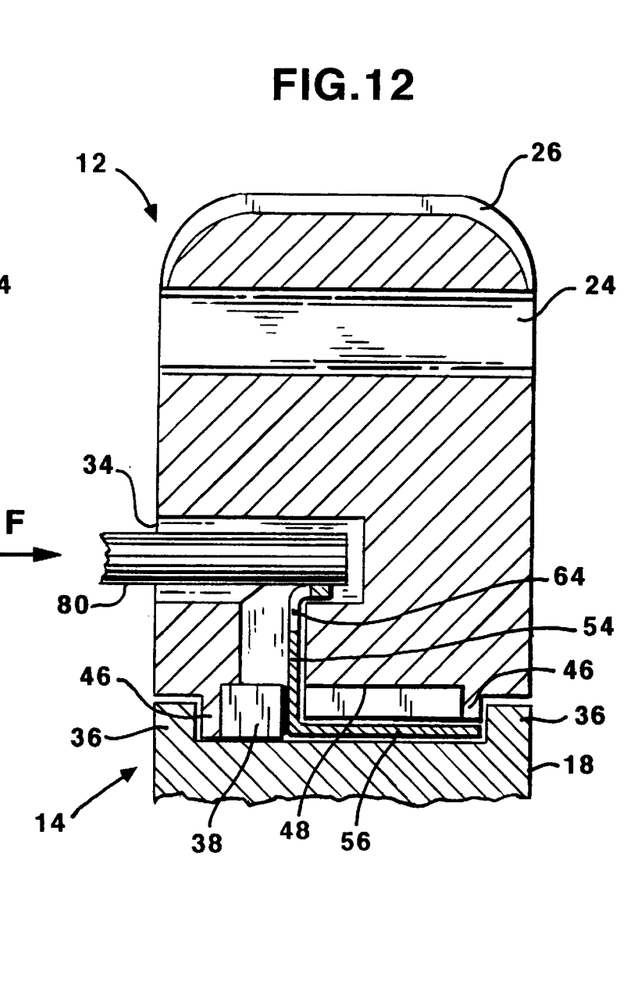
FIG. 12 is a partial side cross-section view of the header module and hermetically sealed enclosure taken along lines 11—11 of FIG. 10 showing the full advancement of the staking tool in the cross-bore and the deformation of the attachment tab.
Figure 13:
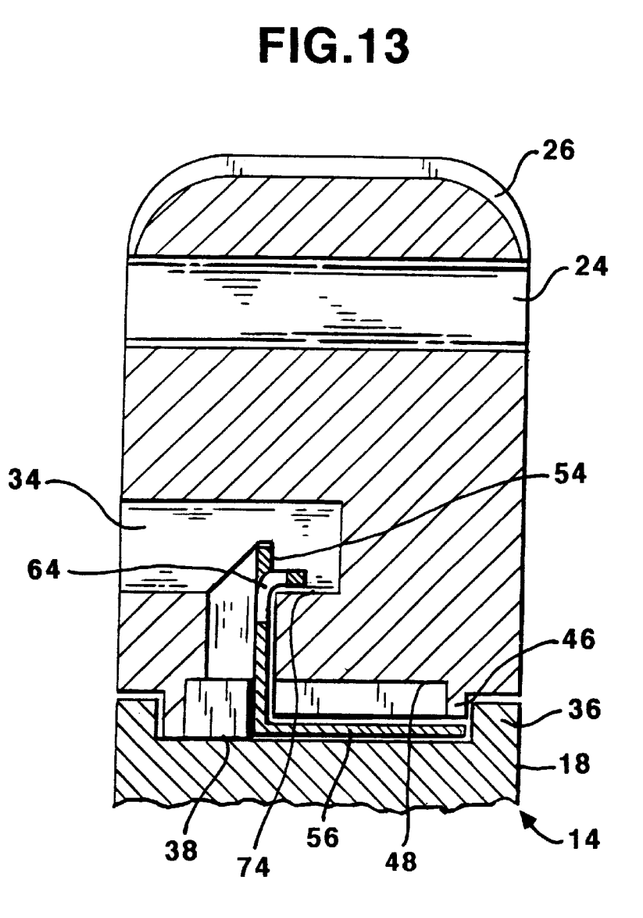
FIG. 13 is a partial side cross-section view of the header module and hermetically sealed enclosure taken along lines 11—11 of FIG. 10 showing the deformation of the attachment tab after withdrawal of the staking tool.

FIG. 12 shows the application of the bending force F through the tool 80 to the bendable member of the upstanding attachment tab 54 to bend it into engagement with the bend engaging portion 74 to attach the pre-formed header module 12 to the hermetically sealed enclosure 14. FIG. 13 shows the resulting deformation of the bendable member. The tool 80 is driven past the tab channel 44 and deforms the free end central portion of the attachment tab 54 that is within the cross-bore 34 so that it extends along the bend engaging portion 74. The side end portions of the attachment tab 54 outside the cross-bore 34 can remain in the tab channel 44. The separation of the side and central portions of the free end of the attachment tab 54 is made easier by the weakening thereof caused by the presence of the tab hole 64, although this may not be necessary in alternative configurations of the cross-bores 32, 34 and the tab channels 42, 44.

Figure 14:
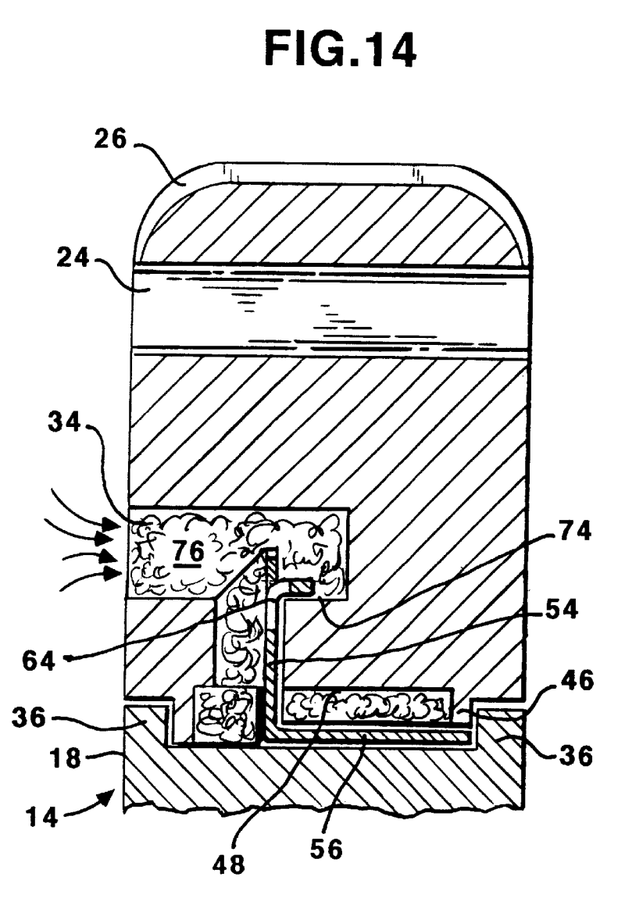
FIG. 14 is a partial side cross-section view of the header module and hermetically sealed enclosure taken along lines 11—11 of FIG. 10 showing adhesive material introduced into the mating attachment surface area through the intersecting cross-bore and tab channel.

FIG. 14 shows the application of adhesive through the access window constituting the cross-bore 34 that flows into the tab channel 44 and into the space between the enclosure attachment surface 38 and the module attachment surface 48. The medical grade adhesive sealing material fills all interior spaces in communication therewith and fills the access window.

Figure 15:
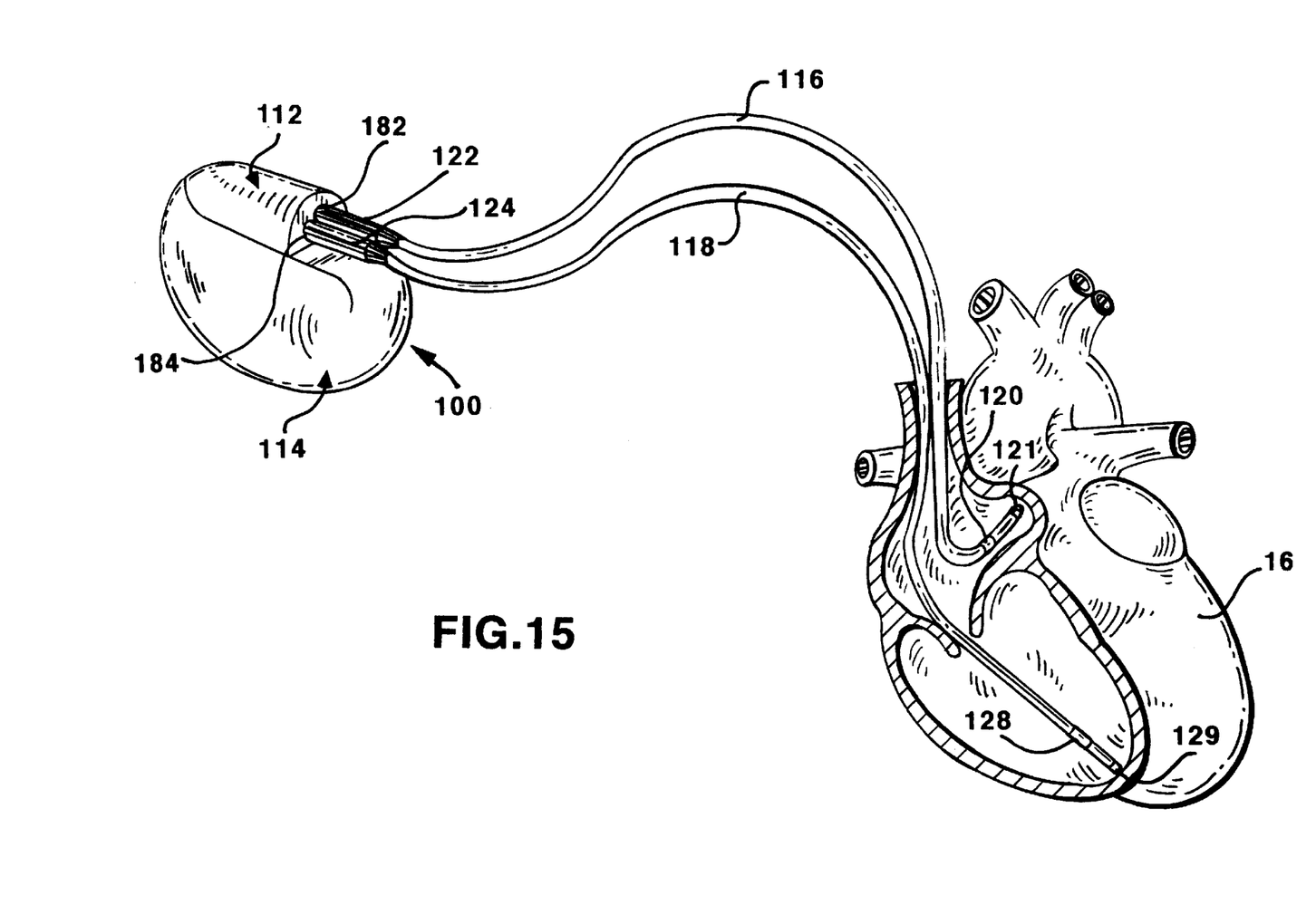
FIG. 15 is an isometric view of a cardiac pacemaker IPG and lead system in relation to a human heart in which the method of the present invention is practiced to attach a connector header module to the hermetically sealed enclosure thereof.
Figure 16:
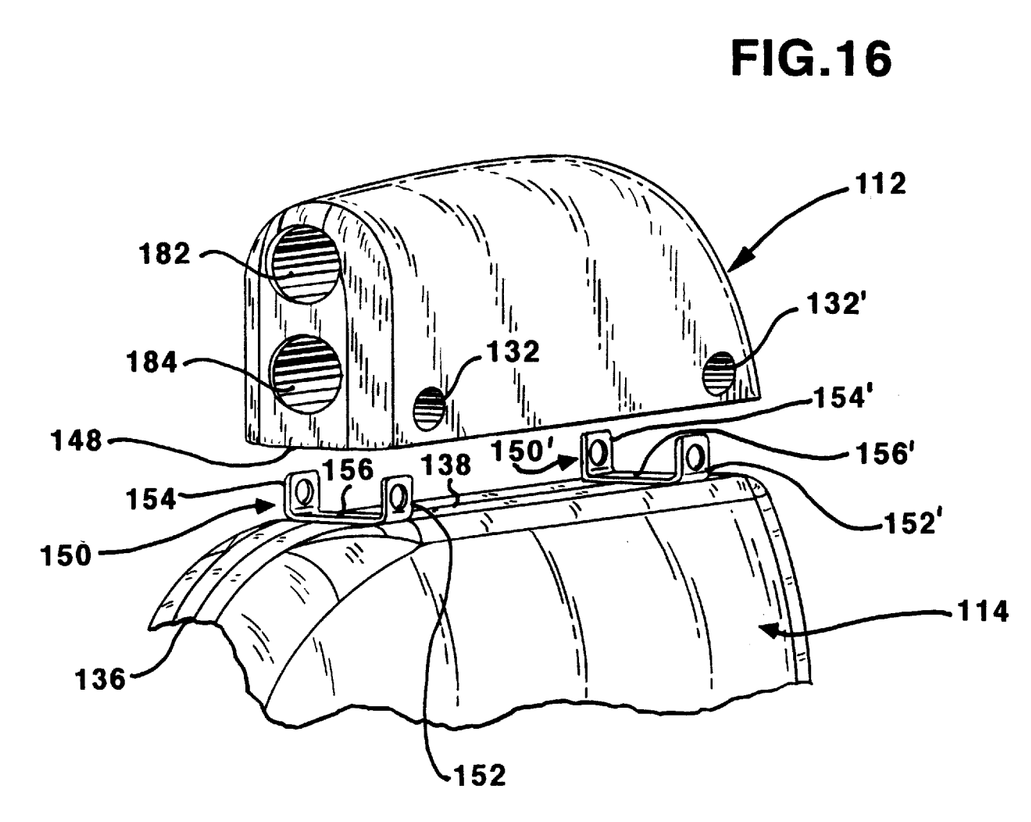
FIG. 16 is a simplified partial exploded isometric view of the connector header module in relation to a set of four upstanding tabs extending upward from the IPG hermetically sealed enclosure housing attachment surface for attachment tin the manner depicted in FIGS. 11–14.

FIGS. 15 and 16 depict the application of the methods and apparatus of the present invention to the attachment of a connector header module 112 to the hermetically sealed enclosure 114 of a dual chamber pacemaker IPG 100. In FIG. 15, the completed dual chamber pacemaker IPG 100 is depicted in an implant relation to a patient's heart 10 wherein atrial and ventricular pacing leads 116 and 118 extend from the connector header module 112 to the right atrium and ventricle, respectively. Atrial electrodes 120 and 121 at the distal end of the atrial pacing lead 116 are located in the right atrium, and ventricular electrodes 128 and 129 at the distal end of the ventricular pacing lead 118 are located in the right ventricle. The connector header module 112 may take any of the forms described above for making the electrical and mechanical connections of the proximal connector end assemblies 122 and 124 of the atrial and ventricular pacing leads 116 and 118 to the electrical circuits within the hermetically sealed enclosure 114. The connector header module 112 therefore incorporates four connector blocks (not shown) within the module housing aligned with the elongated lead connector end receptacles 182 and 184 receiving the lead connector end assemblies 122 and 124, respectively. As in the first embodiment, the header module 112 is molded of a rigid thermoplastic, e.g., a medical grade polyurethane, housing having an exposed module surface and a number of receptacles and channels formed therein. The feedthroughs and feedthrough pins connected to the connector blocks and extending through the hermetically sealed enclosure can are also not shown in FIG. 16 in order to simplify the illustration of the retention structure.

The retention structure and the method of attaching the connector header module 112 to the hermetically sealed enclosure 114 takes substantially the same form and steps as described above with respect to FIGS. 1–14. However, the components of the retention structure are duplicated because of the relatively increased size of the connector header module 112 and the mating module attachment surface 148 and enclosure attachment surface 138. In effect, each end of the elongated connector header module 112 is attached at two laterally displaced points to a respective corner of the enclosure attachment surface 138.

In this embodiment, two duplicate attachment tab assemblies 150,150' that are spaced along the enclosure attachment surface 138 are employed to maximize the attachment peel and pull strength. The attachment tab assemblies 150, 150' comprise upstanding attachment tabs 152 and 154 and 152' and 154 that extend at right angles to opposite ends of attachment tab bases 156 and 156', respectively, and in parallel to one another. Tab bases 156,156' are welded at predetermined locations to a flattened perimeter section of the can, and their exposed surfaces provide part of the enclosure attachment surface 138. The upstanding attachment tabs 152 and 154 and 152' and 154' are therefore opposed to one another across the width of the connector module 112. Each attachment tab 152, 154, 152', 154' also has tab holes formed therein to weaken the central portions of the free ends thereof.

The connector header module 112 is formed with the cross-bores 132 and 132' in the major surface thereof visible in FIG. 16 extending laterally toward the other parallel major surface to intersect the attachment slots therein (not shown) that receive the upstanding attachment tabs 152, 152'. It will be understood that a second set of cross-bores is formed extending laterally in axial alignment with the cross-bores 132, 132' to intersect with the attachment slots therein (not shown) that receive the upstanding attachment tabs 154,154'. Each pair of axially aligned cross-bores may be joined together as a single cross-bore extending from cross-bores 132 and 132' all the way to the other major surface if there is no intervening structure within the connector header module 112 that would be compromised by doing so. The sets of cross-bores and tab channels follow the form of cross-bores 32 and 34 and tab channels 42 and 44 of the first embodiment.

The mating surface configurations of the module attachment surface 148 and the enclosure attachment surface 138 may differ from those of the first embodiment. For example, the module housing surface 148 may be relatively flat except for cut out areas to accommodate feedthrough ferrules and the attachment tab bases 156 and 156'. The hermetically sealed enclosure in the second embodiment is typically formed of mating halves joined together at an overlapping weld seam 136 and the enclosure attachment surface 138 is relatively flat.

The attachment method for attaching the connector header module 112 to the hermetically sealed enclosure 114 is substantially identical to that described above with respect to FIGS. 11–14. The connector header module is seated so that the module attachment surface 148 bears against the enclosure attachment surface 138. The upstanding attachment tabs 152,154 and 152', 154' extend into their respective attachment channels and project into the cross-bores 132, 132' and the axially aligned cross-bores. The steps of bending over the bendable elements of each of the upstanding attachment tabs 152,154 and 152', 154' depicted in FIGS. 11–13 are conducted. Then, the adhesive is applied through the access windows constituting the cross-bores 132, 132' and the axially aligned cross-bores in the manner shown in FIG. 14. The adhesive flows into the tab channels and into the space between the enclosure attachment surface 138 and the module attachment surface 148. The medical grade adhesive sealing material fills all interior spaces in communication therewith and fills the access windows thereto.

A resilient spacer may also be positioned between the module and enclosure attachment surfaces 148 and 138 before the mechanical attachment is effected. Other attachment steps are then completed for attaching feedthrough pins to connector blocks and the like, and any remaining windows may be filled with sealing material.

In both embodiments some curing time is necessary for the adhesive to fully dry, but the assembled cardiac monitor 10 and pacemaker IPG 100 may be handled more freely since the attachment tabs securely hold the components together. The resulting attachment mechanism provides a strong attachment that is not likely to be broken in normal handling and chronic implantation.

In clinical use of the second embodiment, the proximal lead connector end assemblies 122 and 124 are inserted into the elongated lead connector receptacles 132 and 134, respectively, until the lead connector pin or ring is received in the bore of a connector block. The resilient O-ring seals of the lead connector end assemblies 122 and 124 received and compressed in the lead connector receptacles 132 and 134 and aligned connector block bores help to seal the electrical connections from body fluids. Then, each set screw is tightened by a hex wrench pressed through a penetrable silastic septum (which is trapped in the preformed connector assembly housing) into engagement with the head of the set screw to rotate and tighten it to maintain the firm electrical and mechanical attachment.

The above described methods and apparatus for attaching a preformed header module to an implantable hermetically sealed enclosure may be applied to a wide variety of implantable medical devices having a variety of header module and hermetically sealed enclosure configurations. The principals of the present invention may be extended to permutations and combinations of these components of such implantable medical devices.

It should be noted that the term "upstanding" applied to the attachment tabs is intended to convey the meaning that the attachment tabs extend away from the enclosure attachment surface to a point where attachment may be made between a bendable portion thereof and a bend engaging portion of the header module. The attachment tabs need not extend perpendicularly away from the enclosure attachment surfaces or be bent at any particular angle with respect thereto as long as a retention force is achieved therebetween.

Moreover, the number and locations of the upstanding attachment tabs may vary from those depicted in the first and second embodiments. The attachment tabs may also be aligned at angles to one another that differ from the common plane alignment of the first embodiment attachment tabs 52 and 54 and the parallel plane alignments of the second embodiment attachment tabs 152, 152' and 154, 154'. For example, two or more upstanding attachment tabs may be aligned at 90° to one another. Excellent peel and pull strength retention forces can be achieved through judicious selection of the number and locations of the attachment tabs and tab channels.

The preceding specific embodiments are illustrative of the practice of the invention. It is understood therefore that other expedients and equivalents of disclosed components or functions known to those of skill in the art or otherwise disclosed herein may be employed in practicing the invention without departing from the invention or the scope of the following claims.

In the following claims, means-plus-function clauses are intended to cover the structures described herein as performing the recited function and not only structural equivalents but also equivalent structures. For example, although a nail and a screw may not be structural equivalents in that a nail employs a cylindrical surface to secure wooden parts together, whereas a screw employs a helical surface, in the environment of fastening wooden parts, a nail and a screw are equivalent structures.

What is claimed is:

1. A method of making an implantable medical device, comprising the steps of:

providing an hermetically sealed enclosure having an enclosure attachment surface disposed thereon;

providing a pre-formed module having a module attachment surface disposed thereon;

forming a retention structure extending away from the enclosure attachment surface into proximity with a portion of the pre-formed header module when the enclosure attachment surface and the module attachment surface of the pre-formed header module are aligned with respect to one another, the retention structure comprising a bendable member that may be bent from an initial position to allow the pre-formed header module to be seated with respect to the hermetically sealed enclosure in a retention position;

forming a bend engaging portion of the pre-formed header module;

aligning and firmly seating the module attachment surface against the enclosure attachment surface such that bendable member of the retention structure extending away from the enclosure surface is brought into proximity with the bend engaging portion of the pre-formed header module; and applying a bending force to the bendable member to bend it into engagement with the bend engaging portion of the pre-formed header module to attach the pre-formed header module attachment surface to the enclosure attachment surface.

2. The method of claim 1, wherein the retention structure forming step further comprises:

forming an upstanding attachment tab extending from a tab base to a tab free end which constitutes the bendable member; and attaching the tab base at a predetermined location of the hermetically sealed enclosure such that the upstanding attachment tab extends in a predetermined direction away from the enclosure surface and at least a portion of the tab free end is bendable laterally with respect to the predetermined direction.

3. The method of claim 2, wherein the step of forming the bend engaging portion further comprises:

providing a tab channel in the pre-formed header module oriented to receive the upstanding attachment tab when the enclosure attachment surface and the module attachment surface are aligned in respect of one another;

providing an access window extending across the tab channel from a surface of the housing to provide access to the upstanding attachment tab received in the tab channel of the pre-formed header module to define an intersecting edge of the bend engaging portion, wherein the step of applying bending force further comprises applying a bending force to the region of the upstanding attachment tab in the tab channel to bend at least a portion of the tab free end over the intersecting edge of the access window.

4. The method of claim 3, further comprising the steps of:

applying adhesive through the access window to flow into the tab channel; and filling the access window with a sealing material.

5. The method of claim 3, wherein the intersecting access window comprises a cross-bore that extends laterally with respect to the tab channel and the bending force applying step further comprises:

applying a bending force through the access window against the portion of the upstanding attachment tab free end within the window to bend it over the laterally extending intersecting window.

6. The method of claim 5, further comprising the steps of:

applying adhesive through the cross-bore to flow into the tab channel; and filling the access window with a sealing material.

7. The method of claim 3, wherein:

the attachment tab forming step further comprises forming a pair of upstanding attachment tabs extending from each end of the tab base, each attachment tab terminating at its tab free end with a bendable member;

the tab base attaching step further comprises attaching the tab base at a predetermined location of the enclosure attachment surface such that the upstanding attachment tabs extend in predetermined directions away from the enclosure surface;

the tab channel providing step further comprises providing a pair of spaced apart tab channels in the pre-formed header module oriented to receive the upstanding attachment tabs when the enclosure attachment surface and the module attachment surface are aligned in contact with one another;

the access window providing step further comprises providing an access window extending across each of the tab channels to provide access to the upstanding attachment tab received in each tab channel of the pre-formed header module and defining an intersecting edge window in each case;

the aligning and firmly seating step further comprises aligning the module attachment surface with the enclosure attachment surface such that the upstanding attachment tabs are received in the respective tab channels of the pre-formed header module;

the bending force applying step further comprises applying a bending force to each bendable member of each attachment tab in the access window to bend it over the intersecting edge of the access window.

8. The method of claim 7, further comprising the steps of:

applying adhesive through each access window to flow into each tab channel; and filling each access window with a sealing material.

9. The method of claim 1, wherein:

the step of forming a retention structure further comprises attaching a plurality of attachment tabs at a respective plurality of predetermined locations of the hermetically sealed enclosure, each attachment tab extending in a predetermined direction away from the enclosure surface to a tab free end which constitutes the bendable member that is bendable laterally at an angle with respect to the predetermined direction;

the step of forming a bend engaging portion of the pre-formed header module further comprises forming a like plurality of bend engaging portions in the pre-formed header module;

the plurality of bendable members of the plurality of attachment tabs extending away from the enclosure surface being brought into proximity with the respective bend engaging portions of the pre-formed header module in the step of aligning and firmly seating the module attachment surface against the enclosure attachment surface; and the step of applying a bending force comprises applying the bending force to each bendable member to bend it into engagement with a respective proximate bend engaging portion of the pre-formed header module to attach the pre-formed header module attachment surface to the enclosure attachment surface.

10. The method of claim 9, wherein:

the step of forming a like plurality of bend engaging portions of the pre-formed header module further comprises:

forming a like plurality of spaced apart tab channels in the pre-formed header module oriented to receive the upstanding attachment tabs and the bendable members thereof when the enclosure attachment surface and the module attachment surface are aligned in respect of one another; and forming one of the like plurality of bend engaging portions of the pre-formed header module in each of the tab channels; and the step of applying a bending force comprises applying the bending force to each bendable member within each tab channel to bend it into engagement with a respective proximate bend engaging portion to attach the pre-formed header module attachment surface to the enclosure attachment surface.

11. The method of claim 10, further comprising the step of:

providing an access window extending across each of the tab channels to provide access to the upstanding attachment tab received in each tab channel of the pre-formed header module and defining an intersecting edge window for each bend engaging portion; and the bending force applying step further comprises:

applying a bending force to each bendable member of each attachment tab in the access window to bend it over the intersecting edge of the access window, a pair of spaced apart and parallel tab channels in the pre-formed header module being oriented to receive the upstanding attachment tabs when the enclosure attachment surface and the module attachment surface are aligned in respect of one another.

12. The method of claim 11, further comprising the steps of:

applying adhesive through each access window to flow into each tab channel; and filling each access window with a sealing material.

13. An implantable medical device having an hermetically sealed enclosure attached to a pre-formed header module, the device comprising:

a retention structure extending away from the enclosure attachment surface into proximity with a portion of the pre-formed header module when the enclosure attachment surface and a module attachment surface of the pre-formed header module are aligned with respect to one another, the retention structure comprising a bendable member that may be bent from an initial position allowing the pre-formed header module to be seated with respect to the hermetically sealed enclosure to a retention position;

a bend engaging portion of the pre-formed header module over which the bendable member may be bent upon alignment and firmly seating of the module attachment surface against the enclosure attachment surface whereby the bendable member of the retention structure extending away from the enclosure surface is brought into proximity with the bend engaging portion of the pre-formed header module; and a bend formed in the bendable member bending it into engagement with the bend engaging portion of the pre-formed header module to attach the pre-formed header module attachment surface to the enclosure attachment surface.

14. The mechanism of claim 13, wherein the retention structure further comprises:

at least one upstanding attachment tab attached at a tab base to said hermetically sealed enclosure and extending to a tab free end forming the bendable member such that the upstanding attachment tab extends in a predetermined direction away from the enclosure surface and at least a portion of the tab free end is bendable laterally with respect to the predetermined direction.

15. The mechanism of claim 14, wherein the bend engaging portion further comprises:

at least one tab channel in the pre-formed header module, the tab channel being oriented to receive the upstanding attachment tab when the enclosure attachment surface and the module attachment surface are aligned in respect of one another;

an access window extending across the tab channel from a surface of the housing to provide access to the upstanding attachment tab received in the tab channel of the pre-formed header module and defining an intersecting edge of the bend engaging portion;

wherein the bend in the bendable member is formed by applying a bending force to the tab free end in the tab channel to bend at least a portion thereof over the intersecting edge of the access window.

16. The mechanism of claim 15, further comprising:

a layer of adhesive applied through the access window into the tab channel; and a sealing material applied into and filling the access window.

17. The mechanism of claim 15, wherein the intersecting window extends laterally with respect to the tab channel such that the bending force applied through the access window against the portion of the upstanding attachment tab within the window causes the bend to extend over the laterally extending intersecting window.

18. The mechanism of claim 17, further comprising:

a layer of adhesive applied through the access window into the tab channel; and a sealing material applied into and filling the access window.

19. The mechanism of claim 13, wherein the retention structure further comprises:

a pair of upstanding attachment tabs each having a tab free end extending from a common tab base attached to said hermetically sealed enclosure, the tab free ends constituting a respective pair of spaced apart bendable members such that the upstanding attachment tabs extend in predetermined directions away from the enclosure surface and at least a portion of the tab free ends are bendable at an angle with respect to the predetermined direction.

20. The mechanism of claim 19, wherein the bend engaging portions each further comprise:

a tab channel in the pre-formed header module, the tab channel being oriented to receive an upstanding attachment tab when the enclosure attachment surface and the module attachment surface are aligned in respect of one another;

an access window extending across the tab channel from a surface of the housing to provide access to the upstanding attachment tab received in the tab channel of the pre-formed header module and defining an intersecting edge of the bend engaging portion;

wherein the bend in the bendable member is formed by applying a bending force to the free end of the upstanding attachment tab in the tab channel to bend it over the intersecting edge of the access window.

21. The mechanism of claim 20, further comprising:

a layer of adhesive applied through the access window into the tab channel; and a sealing material applied into and filling the access window.

22. The mechanism of claim 20, wherein each intersecting window extends laterally with respect to the respective tab channel such that the bending force applied through the access window against the portion of the upstanding attachment tab free end within the access window causes the bend to extend at least over a portion of the intersecting edge of the access window.

23. The mechanism of claim 22, further comprising:

a layer of adhesive applied through the access window into the tab channel; and a sealing material applied into and filling the access window.

24. The mechanism of claim 13, wherein the retention structure further comprises:

a plurality of upstanding attachment tabs each attached at a tab base to said hermetically sealed enclosure and extending in predetermined directions away from the enclosure surface, the tab free ends of the attachment tabs forming a plurality of spaced apart bendable members that are bendable laterally with respect to the predetermined directions.

25. The mechanism of claim 24, wherein the bend engaging portions each further comprise:

a tab channel in the pre-formed header module, the tab channel being oriented to receive an upstanding attachment tab when the enclosure attachment surface and the module attachment surface are aligned in respect of one another;

an access window extending across the tab channel from a surface of the housing to provide access to the upstanding attachment tab received in the tab channel of the pre-formed header module and defining an intersecting edge of the bend engaging portion;

wherein the bend in the bendable member is formed by applying a bending force to the tab free end in the tab channel to bend at least a portion thereof over the intersecting edge of the access window.

26. The mechanism of claim 25, further comprising:

a layer of adhesive applied through the access window into the tab channel; and a sealing material applied into and filling the access window.

27. The mechanism of claim 25, wherein the intersecting window extends laterally in respect of the tab channel such that the bending force applied through the access window against the portion of the upstanding attachment tab free end within the access window causes the bend to extend over at least a portion of the laterally extending intersecting window.

28. An implantable medical device comprising an hermetically sealed enclosure having an enclosure attachment surface disposed thereon, a pre-formed header module formed of an insulating material and having a module attachment surface disposed thereon, the device comprising:

attachment tab means for extending an upstanding attachment tab in a predetermined direction away from the enclosure attachment surface;

means for defining a tab channel in the pre-formed header module extending away from the module attachment surface and oriented to receive an upstanding attachment tab therein when the enclosure attachment surface and the module attachment surface are seated and aligned with respect to one another;

means for defining an access window extending laterally across the tab channel from a further surface of the pre-formed header module that defines an intersecting edge of the tab channel and exposes a free end portion of the attachment tab within the window extending across the tab channel when the enclosure attachment surface and the module attachment surface are seated and aligned with respect to one another;

wherein the free end portion of the attachment tab is formed with a laterally extending bend thereof over the intersecting edge and into the laterally extending access window so that the attachment tab resists being withdrawn from the tab channel when a separation force is applied to separate the pre-formed header module from the hermetically sealed enclosure.

* * * * *